(12) United States Patent
Azizkhani

(10) Patent No.: US 8,778,421 B1
(45) Date of Patent: Jul. 15, 2014

(54) HERPES TREATMENT

(71) Applicant: Behnam Azizkhani, Esfahan (IR)

(72) Inventor: Behnam Azizkhani, Esfahan (IR)

(*) Notice: Subject to any disclaimer, the term of this patent is extended or adjusted under 35 U.S.C. 154(b) by 0 days.

(21) Appl. No.: 13/739,152

(22) Filed: Jan. 11, 2013

(51) Int. Cl.
*A61K 36/8962* (2006.01)
*A61K 36/00* (2006.01)
*A61K 31/573* (2006.01)

(52) U.S. Cl.
CPC ........... *A61K 36/8962* (2013.01); *A61K 31/573* (2013.01)
USPC .......................................... 424/754; 424/725

(58) Field of Classification Search
None
See application file for complete search history.

(56) References Cited

U.S. PATENT DOCUMENTS

| 4,795,636 | A | * | 1/1989 | Tsuei | 424/754 |
|---|---|---|---|---|---|
| 8,222,299 | B2 | | 7/2012 | Ott | |
| 2003/0077264 | A1 | | 4/2003 | Goodrich | |
| 2007/0154581 | A1 | | 7/2007 | Kumar et al. | |

FOREIGN PATENT DOCUMENTS

| DE | 4024155 A1 | * | 2/1992 |
|---|---|---|---|
| JP | 58067626 A | * | 4/1983 |

OTHER PUBLICATIONS

Batirel et al, Intravenous allicin improves pulmonary blood flow after ischemia-reperfusion injury in rats. The Journal of cardiovascular surgery, (Apr. 2002) vol. 43, No. 2, pp. 175-179.*
G. Goncagul et al., Antimicrobial Effect of Garlic . . . , Journal of Animal and Veterninary Advances, vol. 9, No. 1, pp. 1-4, Jan. 2010.
P. Bergner, *Allium sativum*: Antibiot and Immune Properties, The Healing Power of Garlic, Prima Publishing 1995 currently available on-line at: http://www.medherb.com/Materia_Medica/Allium_sativum_Antibiotic_and_Immune_Properties.htm

* cited by examiner

*Primary Examiner* — Qiuwen Mi
(74) *Attorney, Agent, or Firm* — Frank M. Caprio; Jeremy A. Smith; Bradley Arnat Boult Cummings LLP

(57) ABSTRACT

Herpes infections in human patients can be treated with injections of garlic juice. The garlic juice is produced by cutting, crushing, or otherwise damaging garlic cloves, and collecting the juice. This garlic juice is dissolved in a carrier solution, such as water or saline, and then injected into the patient.

11 Claims, 2 Drawing Sheets ure would likely seek to eliminate or diminish garlic's
effectiveness and ability to heal if man had a relatively
high degree of allergic reactions, or other adverse side
effects, to garlic.

HERPES TREATMENT

BACKGROUND OF THE INVENTION a. Field of the Invention

This invention relates to medical treatment methods and products for various afflictions, including herpes and others.

b. Description of the Related Art

Herpes Simplex Virus

Herpes simplex virus (HSV), Herpesviridae Simplexvirus, is a common virus that can cause many unpleasant and recurrent conditions in humans. HSV can enter the host by direct contact and then spread to target tissues. HSV can target the dorsal root ganglia of neurons, and then remain latent in the targeted tissue. Latent HSV is difficult to target, so a cure of HSV infections is seldom if ever effective, and the vesicles, sores, or lesions can re-appear throughout the infected individual's life.

HSV disrupts host cell molecular functions and host cellular structure, HSV can be manifested clinically as host cellular death, resulting in shallow, painful vesicular ectodermal lesions, but other forms of manifestation are possible. Target tissues for HSV include the skin or mucous membranes, such as the mouth, skin, vagina, conjunctiva, cornea, etc. The virus typically enters the host cell by direct mucosal contact or by direct contact of abraded skin. Once in the skin, the virus replicates in epithelial cells and then enters local sensory neurons. The virus travels to the dorsal root ganglia via retrograde axonal flow where it establishes permanent residency, and establishes latency. Although latent most of the time, it reactivates intermittently, travels down the sensory nerve and causes vesicular eruptions at or near the site of initial invasion. Alternatively the virus may invade the central nervous system and cause encephalitis.

A common manifestation of HSV-1 infection is cold sores, especially in or near the mouth or lips. Herpetic conjunctivitis is a somewhat common disease characterized by swelling and congestion of the palpebral conjunctiva. Keratitis and corneal ulceration may also occur, and herpetic vesicles of the eyelids are typical. Eye lesions typically heal rapidly. HSV-1 can also cause herpes labialis, peri-orbital, perioral, or peri-nasal skin eruptions and, in older patients, the virus has been associated with herpes zoster ("shingles"). Herpes Zoster can cause chickenpox in children and shingles in older patients. Herpes zoster is not HSV-1, but it is a different type of herpesvirus.

HSV-2 causes the most prevalent sexually transmitted disease in the United States, and visits to physicians for genital herpes infections continue to increase. Many Americans are infected with HSV-2. The clinical manifestations range from mild genital inflammation to severe, very painful, vesicular lesions and ulceration. Brain damage and death can result when HSV-2 is acquired by a newborn infant as it passes through an infected birth canal. HSV-2 can also cause cold sores, but this is less common than for HSV-1.

Garlic

Garlic is a plant that has been used for centuries for medicinal and culinary purposes. It is known that garlic has antimicrobial properties, but the exact components or mechanisms of the antimicrobial properties are not certain. Garlic contains many different compounds, including many sulfur compounds such as aliin, allicin, ajoene, allyl propyl disulfide, diallyl trisulfide, s-allylcysteine, vinyldithiins, S-allylmercaptocysteine, and others. Besides sulfur compounds, garlic contains amino acids, minerals such as selenium, enzymes such as allinase, peroxidases, and myrosinase, and other compounds. Garlic contains some volatile oils, and many consider these oils to be responsible for many of garlic's pharmacological properties.

Some attribute the antibacterial activity of garlic to aihcin, which is a sulfur compound. Alliin, which is a non-odoriferous derivative of the amino acid cysteine, is separated from the enzyme alliinase while in a garlic clove. However, when the garlic clove is crushed or damaged, the alliinase can come into contact with the alum to produce the odorous, unstable, water-soluble substance known as allicin (diallyl thiosulphinate).

Allicin decomposes readily to form many different intermediate products. The allicin degrades at room temperature, and the rate of degradation increases with increased temperatures. The degradation products of allicin are generally not believed to have significant antimicrobial properties. Therefore, the antimicrobial properties of garlic may be adversely impacted by extended storage or high temperatures. Ajoenes and dithiins are also found in crushed garlic, and have been demonstrated to have antimicrobial properties.

Many compounds can act together to produce a desired effect, and the various antimicrobial properties of garlic may be the result of several compounds working in concert. Some of the various compounds may work together to combat certain microbes, and various microbes might be inhibited by different compounds or combinations of compounds in garlic.

BRIEF SUMMARY OF THE INVENTION

Herpes infections in human patients can be treated with injections of garlic juice. The garlic juice is produced by cutting, crushing, or otherwise damaging garlic cloves, and collecting the juice. This garlic juice is dissolved in a carrier solution, such as water or saline, and then injected into the patient.

DETAILED DESCRIPTION OF THE INVENTION

Figure 1:
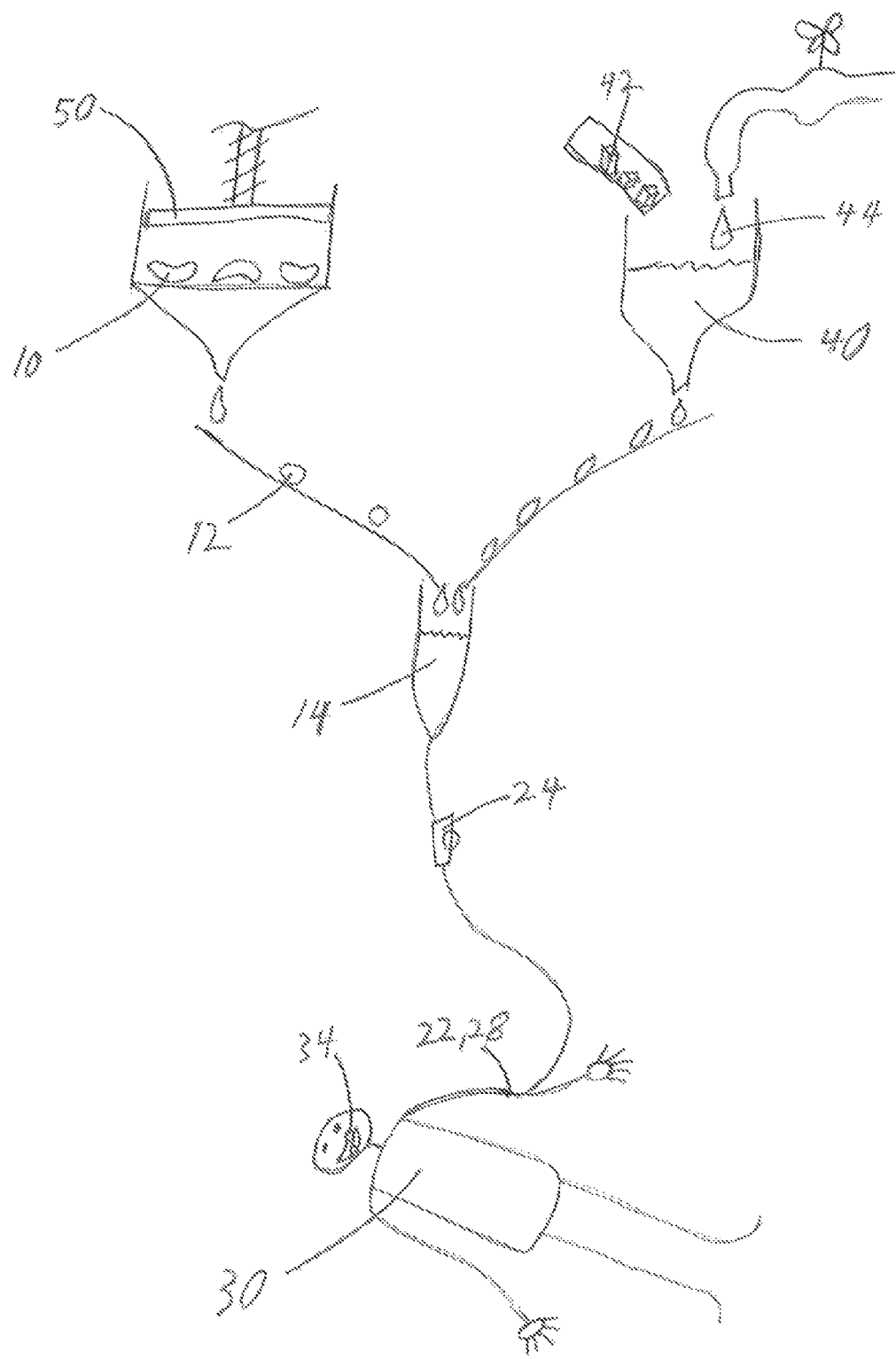
FIG. 1 is a diagram depicting the creation of a garlic solution, and an intravenous (IV) injection of that garlic solution into a patient.
Figure 2:
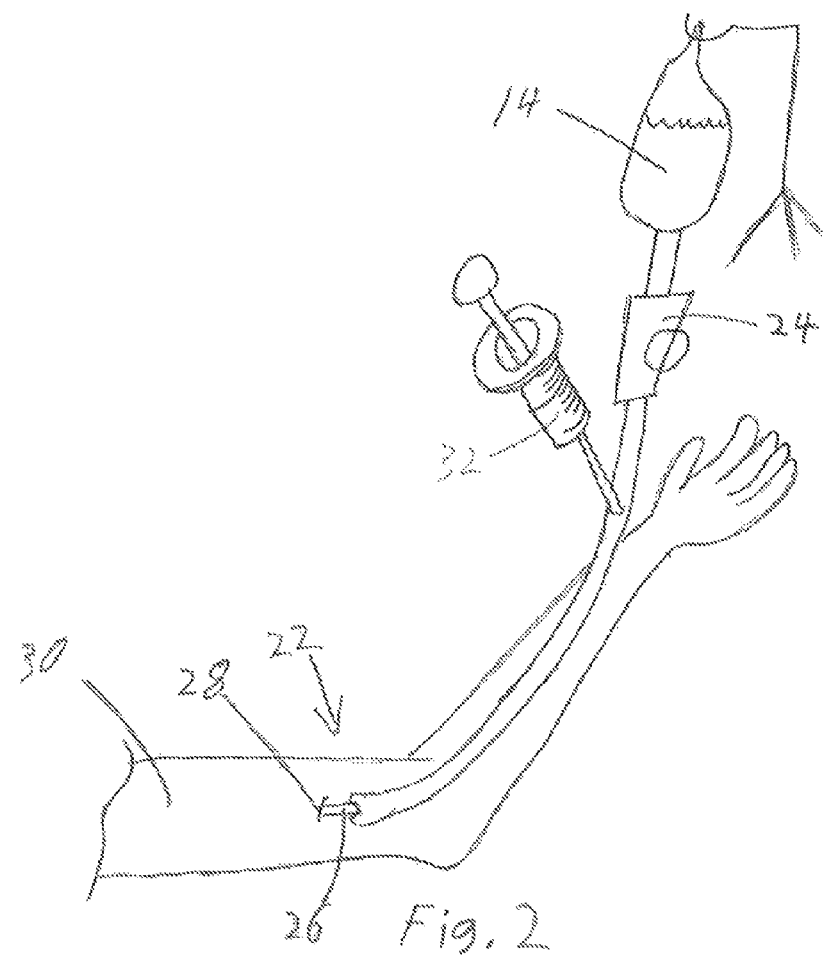
FIG. 2 is a diagram of an IV injection of garlic solution into a patient.
Figure 3:
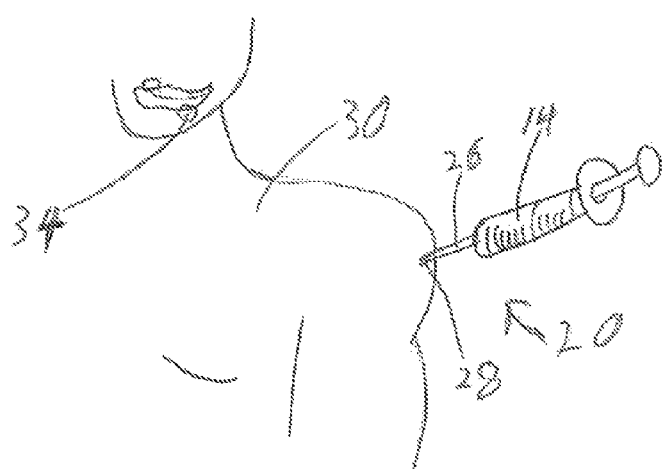
FIG. 3 is a diagram of an intramuscular injection of garlic solution into a patient.

The use of injections of a garlic solution has been found to aid in the treatment of many conditions or ailments, as illustrated in FIGS. 1-3. The current inventor has primarily tested and experimented with treatments for herpes infections, but the inventor has conducted tests that show injections of garlic solution 14 does have therapeutic benefits for many other conditions. All testing described herein was performed in Iran on volunteer patients who were informed of the risks involved, and who freely elected to participate in the inventor's studies.

Garlic 10 is a naturally occurring product, and mankind has been consuming and using it for many years. Therefore, the chances of adverse side effects from the use of garlic 10 seem remote, especially when compared to synthetic compounds or other compounds with less history of use by man. Mankind's long history with garlic 10, the fact that garlic 10 is a natural product, and the fact that garlic 10 has known antimicrobial properties inspired the inventor to investigate the use of garlic 10 to treat herpes and other conditions.

Injection Considerations

Cloves of garlic 10 comprise a multitude of different chemical compounds, similar to many other plants and living organisms. It may be possible to isolate one or a limited selection of chemical compounds present in garlic 10 to achieve the same or similar results as described below, and it may even be possible to synthetically produce the compounds needed. The inventor has discovered useful and beneficial therapeutic uses for garlic 10 which may derive from a limited number of chemical compounds within garlic 10, but the specific compounds of interest for the uses described have not been identified or isolated for this disclosure. Therefore, this disclosure describes direct extraction and use of compounds from garlic 10, but it is understood that isolated compounds present in garlic 10 may give comparable results. It is also understood that removal of selected compounds from garlic 10 before injection may be beneficial, especially if the patient 30 has known allergic reactions to specific garlic compounds.

Herpes or other infections can be present at specific, discrete locations within the human body, and the method of treatment needs to be able to reach the pathogens to treat them. When garlic juice 12, or any other substance, is injected into the bloodstream it rapidly reaches essentially all parts of the body where the herpes virus may be located. Therefore, an injection into the bloodstream can eradicate the herpes virus wherever it is located, even if the virus is in "hidden" locations such as a nerve ganglion, and even when the virus is dormant. The blood also circulates by herpes blisters so the garlic components can be delivered to herpes virus within or near the blisters. The bloodstream reaches all these locations, so injecting garlic juice 12 provides an effective means to expose the virus to the garlic components. For the same reasons, injection of garlic juice 12 can also be effective for many other types of infections, such that the treatment method described can be used for conditions other than herpes.

Humans have many natural defenses from the environment at large. For example, the skin is a formidable barrier that prevents most compounds and materials in the environment from entering the body. The stomach and gastrointestinal tract also serve to block many compounds and materials from entering the body. For example, stomach acid may change a compound before it can be absorbed into the blood stream, and the gastrointestinal walls can selectively block certain compounds or materials from entering the blood stream. Animals have similar defenses, and this description is also applicable to animals other than humans.

Tests described below have shown that oral or topical application of garlic 10 does not provide the same benefits and results as injection of the garlic 10. Therefore, it appears some of the beneficial compounds in garlic 10 are not entering the blood stream through oral or topical use, so the natural defenses of the body must be blocking some compounds out or changing those compounds before they enter the blood stream.

An injection puts all the compounds in the garlic juice 12 directly into the blood stream, so the natural defenses in the skin and gastrointestinal tract are by-passed. This allows the garlic juice 12 to reach the infection source in the body by way of the blood stream. The initial concentration of the garlic compounds is also increased in an injection, because the entire solution enters the blood stream instead of selected compounds absorbing over time, ingestion may expose the components of garlic to enzymes or other compounds, which may speed the degradation process and may cause the desired compounds to degrade before entering the blood stream. These are some of the reasons that may explain why injecting the garlic juice 12 has better results than ingestion or topical application.

The injection also puts all the compounds in the garlic juice 12 into the blood stream at the same time, and there could be varying absorption rates for different compounds through the skin or gastrointestinal tract. Some components in garlic 10 degrade fairly rapidly, and the use of injections serves to rapidly and simultaneously introduce all the compounds at one time. If more than one compound work together to produce a desired antimicrobial effect, and one or more of the responsible compounds degrades over time, then simultaneously adding all the compounds may improve the effectiveness because the desired compounds are present at the same time. Further degradation of the various garlic compounds may or may not proceed within the blood. The blood stream then distributes the components of the garlic juice 12 to the entire body.

The inventor discovered that injections of high concentrations of garlic juice 12 were very painful, so it is preferable to dilute the garlic juice 12 in a solvent of some type. Initial testing with pure garlic juice 12 or garlic juice 12 diluted with a relatively small amount of solvent caused inflammation and soreness at the injection site 28. For example, injections of a garlic solution 14 comprising approximately 25% garlic juice 12 and 75% solvent were very painful, so higher dilutions are preferred. When the garlic juice 12 was diluted and injected more slowly by IV, the injection pain was significantly reduced, and there were no notable signs of adverse bodily functions. Most of the successful injections used a solution of no more than 1% garlic juice 12 in a solvent, and the solvent used was normal saline. It is preferable to use normal saline 40 or other injection fluids when large quantities of liquid are injected, as opposed to injecting large quantities of water 44, because the saline 40 or injection fluid more closely match the density of blood serum.

The relatively low concentration of garlic juice 12 in the garlic solution 14 means that a relatively large quantity of liquid should be injected into the patient to introduce the desired quantity of garlic juice 12. Intramuscular (IM) injections 20 were performed on some animals, and the results indicate an IM injection 20 would suffice for introducing the garlic 10 to the patient 30. However, IM injections 20 are not well suited for introducing large quantities of fluid, and IM injections of garlic solution 14 are very painful, even when using concentrations as low as 1%. An intravenous (IV) injection 22 can be set up to gradually introduce fluids into a person over an extended period, such as over several hours, and IV injections of garlic solution 14 are much less painful than IM injections, even when using the same concentration. The rate of an IV injection 22 can be controlled with a flow controller 24, so the rate of addition can be set as desired. Therefore, most of the experimental tests used IV injection 22. However, initial testing indicates IM injection 20 would also work, but most likely with a noticeably higher level of pain.

It is possible to use additives or other compounds to facilitate the injection. For example, hydrocortisone 32 can be injected prior to, or with, the garlic solution 14 to help control allergic reactions and to minimize the Chances of the patient entering shock. The hydrocortisone 32 can be injected at the same location as the garlic solution 14, and even using the same injection needle 26. The highest blood concentrations of hydrocortisone 32, garlic solution 14, or any other compound are present at the injection site 28, and the injected compounds are then diluted and distributed by the blood. Introducing the hydrocortisone through the same hypodermic injection needle 26 as the garlic juice 12 will minimize the number of injections given to the patient 30, as well as putting the highest concentration of hydrocortisone 32 at the point with the highest concentration of garlic solution 14. However, other injection sites 28 for hydrocortisone 32 would likely be effective as well.

The hydrocortisone 32 is preferably injected before the garlic juice 12 for a few reasons, but it may be possible to combine the hydrocortisone 32 and garlic juice 12 in some embodiments. Injecting the hydrocortisone 32 before the garlic juice 12 allows the hydrocortisone 32 to enter the blood to take effect and help prevent shock before the first garlic juice 12 is injected. It also allows the full quantity of hydrocortisone 32 to be in the patient's body before any of the garlic juice 12 is added, and it also minimizes the chances of a reaction between the hydrocortisone 32 and any of the components of the garlic juice 12. The hydrocortisone 32 should not be injected more than 24 hours before the garlic juice 12, so it remains effective. Hydrocortisone 32 injection times of only 1 or 2 minutes before the garlic juice 12 injection would most likely be effective, but essentially any time up to when the hydrocortisone 32 is no longer effective should also work.

An injection of hydrocortisone 32 would normally be expected to inflame a herpetic outbreak, because the hydrocortisone 32 is immunosuppressive. However, the antimicrobial effects of the garlic solution 14 were found to far outweigh the immunosuppressive effects of the hydrocortisone 32, so there was no noticeable decrease in effectiveness for a garlic solution injection when hydrocortisone 32 was also used.

Several possible variations for the injection of the garlic solution 14 are possible. For example, alcohol could be added to the solvent to help dissolve oils in the garlic liquid 12, or art antithetic could be added to reduce pain. Other modifications or changes could also be made.

Garlic Solution Preparation

The preparation of the garlic solution 14 is relatively simple. Normal saline 40 was selected as the solvent because normal saline 40 is the simplest solution for IV injections. Normal saline 40 is made by mixing sodium chloride 42, which is common table salt 42, with water 44. The salt 42 dissolves in the water 44 to make a solution, and this solution is typically sterilized before use. Normal saline 40 has a concentration of about 0.9% sodium chloride 42, but the exact concentration is not critical. The concentration of salt 42 in normal saline 40 could vary, such as between 0.7% and 1.1%, or between other concentrations, and it is unlikely there would be any significant adverse effect on the patient 30. Other solvents could also be used. For example, low quantities of ethanol could be added to the water 44, which may improve the dissolution of some of the oils in the garlic juice 12. There are many injection fluids available, and these injection fluids are probably suitable for use as the solvent. The solvent should be something that is not toxic, and something that readily dissolves garlic juice 12. Side effects of any compounds added to the garlic solution 14 should also be considered. The efficacy of the treatment depends on the amount of garlic juice 12 injected, and not on the amount of solvent, but the concentration of the garlic solution 14 does impact the comfort of the treatment.

The garlic juice 12 was prepared by squeezing and/or cutting the raw cloves of garlic 10. This can be done in a press 50, a juicer, a mortar and pestle, a simple knife, or other techniques. The garlic 10 is squeezed, smashed, cut up, or damaged in some way, and the garlic juice 12 is collected. The garlic, cloves 10 were sterilized before the garlic juice 12 was collected, to reduce the chances of infection. Heat can adversely impact the antimicrobial properties of garlic 10, so the garlic cloves 10 were sterilized chemically instead of thermally. This can be done with hydrogen peroxide or bleach, but other chemical compounds could be used. For example, methyl alcohol, ethyl alcohol, iso or n propyl alcohol, other alcohols, iodine, formaldehyde or other aldehydes, iodophors, or quaternary ammonium compounds could be used, amongst others.

The garlic 10 should not be excessively heated before use, so heat for sterilization or other purposes should be avoided. Garlic 10 is commonly kept at room temperature, and garlic 10 kept at room temperature was effective, so there is no need to refrigerate the garlic 10. The garlic 10 used in the experiments was fresh, but aged garlic 10 would also likely work. The garlic 10 should be raw garlic 10, as opposed to cooked or cured garlic 10, to retain as many natural compounds as possible. Also, the garlic 10 should not be dried, because there will be little or no garlic juice 12 in dried garlic 10, and some of the natural compounds may have started to break down or degrade.

Once the garlic juice 12 is extracted from the sterilized garlic cloves 10, it is added to the normal saline 40, other injection fluids such as albumin or dextrose solutions, or some other solvent. The garlic juice 12 should be filtered to remove particulates, because particulates interfere with injections, and particulates are poorly received in the circulatory system. The garlic juice 12 can be filtered with standard filter paper, preferably sterile filter paper, but other filter media can be used. The garlic juice 12 can be filtered before being added to the solvent or after, and it can be filtered more than once. The garlic juice 12 is dissolved in the solvent by simple mixing, and the result is the garlic solution 14. The resulting garlic solution 14 should be used relatively quickly, because some of the garlic compounds degrade over time. Garlic solution shelf life would likely increase if stored at lower temperatures. Storage times at room temperature of at least 1 hour after the garlic juice 12 is extracted from the garlic 10 are acceptable, as verified by the testing.

Based on reported information for garlic 10, it is believed that allicin, ajoenes, and diallyl disulfide have the most significant effects on infections, but it also seems likely that more than one different components of garlic act together in a synergistic fashion to combat infections.

Treatment Procedure

The herpes treatment procedure is relatively simple. The first step is to find a person with herpes who needs treatment, and that person becomes the patient 30. The treatment is completed by obtaining a garlic solution 14, and injecting the garlic solution 14 into the patient 30. The effects on the treatment were most visible when the patient had active herpes vesicles 34, and the tests were primarily directed towards both oral and genital vesicles 34. A herpetic infection is said to be active when the infected person has sores or vesicles. Testing indicates the treatment is effective for both active and inactive herpes infections, especially the recurrent herpetic whitlow tests described below. Inactive herpes is not visible, so test results are difficult to measure. The treatment did stop the active herpes, and speed the recovery, but at least some patients 30 did have subsequent outbreaks of vesicles 34 which are thought to be due to re-infection, not recurrence, because the human immune system cannot create a complete and permanent immunity against herpetic infection.

The treatment also appears to cure recurrent herpetic whitlow, where the vesicles 34 were located on the patient's fingers. The cure seems to be complete, with no recurrent outbreaks. The fingers are not the preferred location for the herpes simplex virus, so re-infection after the treatment is less likely on the fingers.

The method was also found to be effective in treating malaria. The garlic juice injections were repeated for 4 days to cover the reproduction cycle of the malaria parasite in the patient 30. The test subjects were given 1 injection per day for 4 consecutive days, but increased or decreased frequency may also be possible.

The method was also effective at treating antibiotic resistant bacterial infections, at least including kidney and urinary tract infections. The treatment involved IV injections of garlic solution 14 for 3 consecutive days, and urethra injections into the bladder and urethra for 2 consecutive days. It is expected that other antibiotic resistant bacterial infections could also be effectively treated.

In general, the garlic juice 12 was diluted in normal saline 40 to a concentration of 1% or less, so at least 100 cubic centimeters (cc) of normal saline 40 were used for 1 cc of pure garlic juice 12. The density of normal saline 40 is slightly greater than 1 gram per cubic centimeter (g/cc), and the density of pure garlic juice 12 is about 1.03 g/cc, so the garlic solution 14 can comprise about 100 grams of water/saline per gram of garlic juice 12. This concentration is not critical, but it does appear to provide good results. 0.065 grams (g) of garlic juice 12 were used for 1 kilogram (kg) of the patient's weight. Therefore, a patient weighing 10 kg would receive a total of 0.65 grams of pure garlic juice 12, plus at least about 65 grams of normal saline 40, in a standard injection. The solvent or saline 40 are used to facilitate the injection and control pain, but the amount of solvent and the concentration of the garlic solution 14 does not impact the efficacy of the treatment as long as the total quantity of garlic juice 12 injected remains sufficient. These dosages and ratios applied for almost all the different conditions tested. The amount of garlic juice 12 injected per weight of the patient 30 could be varied as well, but the 0.065 g garlic juice 12 per kg of patient weight was found to be effective. The quantity described seemed sufficient, because repeated injections were not required for most conditions, and the patients 30 tolerated the injections well so the quantity does not seem excessive. Also, the inventor noticed proportional treatment effects for smaller quantities of garlic juice 12.

Treatment with garlic 10 may also be a valuable veterinary medicine for many ailments of livestock or other animals, including foot and mouth disease, bronchitis, and others. Garlic 10 is relatively inexpensive and readily available, which makes its use more economical than some other treatment options. IV or IM injections of garlic 10 have greater effectiveness than oral or topical applications for livestock as well, Results and Testing Many tests were performed to verify the effectiveness of garlic as a treatment for herpes and other afflictions. All tests were conducted in Iran in accordance with local laws,
1. Topical Results, Human Trials Tables 1 and 2 show the results of topical application of garlic to herpes simplex lesions. These tests were completed in March of 1993. In these tests, the human patients were from 20 to 50 years old, and all were assessed to verify they had no systemic diseases. The patients were brought in on the first day of manifestation of blisters. The first patient to visit was identified as Patient #1, the second patient to visit was identified as Patient #2, and so on. Odd numbered patients were treated with garlic, and became the experimental group, and even numbered patients were not treated at all and were used as a control group.

The experimental group was treated by rubbing cut garlic on herpetic blisters, so the garlic was applied externally or topically. The cut garlic was applied three times on the first day, and there were no subsequent treatments. The patients in both the experimental and control group were observed, and the results are shown in Tables 1 and 2, below.

TABLE 1

External use of cut garlic rubbed on the affected area

| Patient # | Age in years | Gender | Hours after application for blister to become turbid | cessation of blister growth after the first external use | Hours after application for reported reduction of itching and burning | Days for crusts to fall off after treatment | Days from blister manifestation to crusts falling off |
|---|---|---|---|---|---|---|---|
| 1 | 36 | M | 4 | Immediate | 1 | 4 | 5 |
| 3 | 32 | F | 5 | Immediate | 2 | 4.5 | 6.5 |
| 5 | 45 | M | 4 | Immediate | 1 | 5 | 6 |
| 7 | 27 | F | 6 | Immediate | 0.5 | 3 | 3.5 |
| 9 | 43 | F | 5 | Immediate | 1 | 4 | 5 |
| 11 | 37 | F | 5 | Immediate | 1 | 4 | 5 |
| 13 | 34 | M | 6 | Immediate | 1 | 4 | 5 |
| 15 | 25 | F | 4 | Immediate | 0.5 | 3 | 3.5 |
| 17 | 33 | F | 6 | Immediate | 0.5 | 4 | 4.5 |
| 19 | 38 | M | 5 | Immediate | 1 | 4 | 5 |
| 21 | 41 | F | 7 | Immediate | 0.5 | 4 | 4.5 |
| 23 | 21 | M | 4 | Immediate | 0.5 | 3 | 3.5 |
| 25 | 24 | F | 5 | Immediate | 0.5 | 4 | 4.5 |
| 27 | 32 | F | 7 | Immediate | 1 | 3 | 4 |
| 29 | 20 | F | 4 | Immediate | 0.5 | 3 | 3.5 |
| 31 | 28 | M | 5 | Immediate | 1 | 4 | 5 |

TABLE 1-continued

External use of cut garlic rubbed on the affected area

| Patient # | Age in years | Gender | Hours after application for blister to become turbid | cessation of blister growth after the first external use | Hours after application for reported reduction of itching and burning | Days for crusts to fall off after treatment | Days from blister manifestation to crusts falling off |
|---|---|---|---|---|---|---|---|
| 33 | 47 | M | 7 | Immediate | 1 | 4.5 | 5.5 |
| 35 | 22 | F | 5 | Immediate | 0.5 | 4 | 4.5 |
| 37 | 34 | F | 7 | Immediate | 0.5 | 3 | 3.5 |
| Mean | | | 5.3 | Immediate | 0.82 | 3.79 | 4.61 |

TABLE 2

Control group, no garlic applied to patient

| Patient # | Age (years) | Gender | Days from manifestation of blisters to cessation of growth | Days from manifestation for crusts to fall off |
|---|---|---|---|---|
| 2 | 24 | F | 4 | 11 |
| 4 | 31 | F | 5 | 14 |
| 6 | 22 | M | 4 | 10 |
| 8 | 43 | F | 4 | 11 |
| 10 | 37 | M | 3 | 8 |
| 12 | 31 | M | 4 | 9 |
| 14 | 38 | M | 4 | 11 |
| 16 | 47 | F | 5 | 13 |
| 18 | 20 | F | 3 | 7 |
| 20 | 34 | M | 4 | 12 |
| 22 | 27 | F | 4 | 11 |
| 24 | 33 | F | 4 | 11 |
| 26 | 39 | M | 5 | 14 |
| 28 | 26 | F | 3 | 9 |
| 30 | 36 | F | 3 | 9 |
| 32 | 21 | F | 4 | 10 |
| 34 | 30 | M | 3 | 8 |
| 36 | 32 | M | 4 | 11 |
| Mean | | | 3.8 | 10.5 |

Patients in the experimental group reported burning for a few minutes after application of the garlic, but then they felt better and reported reduced burning and itching. Within about 5 to 7 hours, the fluid in the blisters for the experimental group changed from clear to a semi-clear or cloudy appearance. In the control group, some blisters would become cloudy while other blisters in the same area were growing and clear, so it was difficult to specify when the blisters became cloudy. In the experimental group, all the blisters became cloudy very shortly after application of the garlic, so it was possible to identify when the blisters became cloudy. No growth or extension of the blisters was observed in the experimental group after application of the garlic, and the blisters rapidly started to become wrinkled in appearance, as well as shrinking and becoming dryer. Therefore, the cessation of growth of the blisters, after application of the garlic, was recorded as "immediate." For the experimental group, the time period from manifestation of the vesicles (also referred to as blisters) to the final crusts failing off was from 3.5 to 6.5 days. However, after a period of months, some patients from the experimental group manifested new blisters, and often in the same site as the blisters that were treated with garlic.

In the control group, the blisters grew and extended for about 3 to 5 days, after which time the patients reported a gradual decline of the burning and itching sensations. After the blisters stopped growing and the burning and itching sensations declined, the blisters began to become wrinkled and dryer in appearance. The total elapsed time from manifestation of the blisters until the crusts fell off ranged from 7 to 14 days, which is notably longer than for the experimental group. The control group also manifested recurring blisters, which were often in the site as the previous blisters. Topical treatment with garlic appears to stop blister growth, but have no impact on recurrent outbreaks. Therefore, it appears that external or topical application of garlic can treat herpes blisters or outbreaks, but it does not cure the disease or eradicate the herpes virus from the body.

2. Injection Results, Animal Trials

Injections of garlic were examined after the topical applications, because some of the components in the garlic would likely be blocked from the blood stream by the gastrointestinal tract, and other components may be changed before entering the blood stream. Initial tests were done on animals.

The first clinical trial was performed on 200 chickens in June of 1993. There were 100 chickens in a control group and 100 chickens in an experimental group, and all chickens were about 850 grams and 42 days old. Injections were intramuscular (IM), and each chicken in the experimental group received 0.6 cubic centimeters (CC) of a 30% garlic solution. A 30% solution means the solution comprised 30% pure garlic juice, and 70 percent normal saline. Each chicken in the experimental group was injected with 0.6 cc of the 30% garlic solution three times, where the injections were given two days apart such that all three injections were completed over approximately 96 hours. The control group was not given any injections.

The experimental and control groups of chickens were kept separate, but in similar coops with similar conditions. A veterinarian controlled the chickens, and they were observed regularly over a two month observation period for vital signs, feeding habits, motion, and general observations by the veterinarian. The veterinarian was of the opinion that the experimental group was in at least as good health as the control group, and the experimental group even appeared to be somewhat healthier. The mortality rate for the experimental group was 3% less than the control group, and the experimental group had more overall weight gain during the observation period.

A random selection of 25 chickens from each of the experimental and control groups were dispatched and evaluated for pathological changes. No pathological differences were noted between the two groups. This test was repeated a second time, with the only difference being the garlic solution was injected intravenously (IV) with an insulin syringe into the vein under the wing. The results were the same as the first test.

Additional tests were performed on other animals, including rabbits, sheep, goats, and cows. Each animal was injected with 0.6 CC of 16.7% garlic solution per kilogram of weight for the animal, so each animal was injected with a total of 0.1 CC of garlic juice per kilogram of weight. Garlic juice has a density of approximately 1.03 grams per cubic centimeter (g/cc). All injected animals were observed for some time, and no mentionable problems were noted. Some injections were done on pregnant animals, and the offspring were then examined. In each case, the offspring was healthy and no health problems, birth defects, low birth weights, or other issues or problems were noticed in the offspring.

Some cows injected with foot and mouth disease were injected with 0.065 cc of garlic juice per kilogram of weight, where the garlic juice was diluted in 2 liters of normal saline, and all the cows rapidly overcame the foot and mouth infection. No control group was used with these cows infected with foot and mouth disease. In a separate test, 9 sheep infected with bronchitis were injected with garlic solution. All 9 sheep had lost their wool, were very thin, and one of the sheep was pregnant. Each sheep was injected with 0.065 cc of garlic juice per kilogram of weight of the animal on 3 separate occasions, with a 2 day interval between the injections. All of the sheep gained weight, grew wool again, and the pregnant sheep gave birth to a healthy, fat lamb.

3. Injection Results, First Human Trials on the Inventor

After reviewing the results from the tests on the animals, the inventor decided to try an IV injection of garlic solution on himself as an initial human trial. The first trial was performed on Mar. 29, 1996, and a syringe was filled with 25 cc of garlic solution, where the garlic solution was made from 5 cc of pure garlic juice and 20 cc of normal saline. The inventor injected 0.5 cc of the garlic solution directly into his vein and noticed a very biting and sharp pain that started at the injection point and followed the path of the vein to the inventor's heart. The inventor waited several minutes, and then mixed the remaining 24.5 cc of garlic solution into 500 cc of normal saline, and then continued injecting the diluted garlic solution over the course of 2 hours.

The inventor monitored his vital signs during the injection of garlic solution, including his blood pressure, breathing, heart rate, and temperature. The inventor also tested his complete blood count (CBC), serum glutamic oxaloacetic transaminase (SGOT), and serum glutamic pyruvate transaminase (SGPT) tests both before the injection, and 16 hours after the injection. The inventor noted his heart beat increased to 110 to 115 beats per minute after the initial (high concentration) injection, and this condition continued for approximately 4 hours after finishing all the injections. The inventor's SGOT test before the injection was within the normal range of 0-37, and 16 hours after the injection the SGOT test increased to 43. The inventor's SGPT test before the injection was within the normal range of 0-41, and 16 hours after the test the SGPT was 57. The inventor repeated these tests 3 days after the injection, and all the results were within the normal ranges and were almost the same as before the injection. The inventor's weight was approximately 70 kilograms (kg) for the entire test period described herein.

Nine hours after the injection, the inventor felt pain beginning at the point where the injection was made along the vein in the inventor's forearm, and the skin was red and inflamed for about 25 centimeters (cm) on this route. Four days after the injection, the inventor's arm was no longer sore, red, or inflamed, and these conditions did not re-appear. The inventor also had a mild headache and mild nausea after the injection, but the headache stopped 2 days after the injection and the nausea stopped about 6 hours after the injection. For 4 days after the injection, the inventor noticed reduced pains along the route of the injection vein when waking in the morning as compared to when he went to bed the previous night.

Before the injection, the inventor had acute herpetic gingivostomatitis on the left side of his hard palate, with soreness. The inventor noticed the associated burning and pain were gone within 6 hours of the injection, and 2 days after the injection the inventor was asymptomatic. The inventor experienced vertigo, with unknown etiology, for several years before the injection. The inventor had noticed his vertigo was present in both the standing and laying positions and the vertigo became worse when he caught a cold. When the inventor shook his head the vertigo became worse and he became nauseated. The inventor noticed a gradual decline in his vertigo over the 3 months after the injection, and the vertigo was completely absent 3 months after the injection. The inventor did a second injection 2 months after the first, as summarized below.

The inventor completed several IV injections into himself after the first one, as summarized below. In these tests, the garlic solution was injected over a 5 hour period, the garlic was more dilute than the initial 0.5 cc injection, and there was no phlebitis (redness or soreness of the injection vein), and no sign of any allergic reaction or shock,

| Inventor Self-Injection Schedule. | | |
|---|---|---|
| Date | cc garlic juice/<br>cc normal saline | Comments |
| 29 Mar. 1996 | 5/520 | Started at 5/20 garlic to normal saline |
| 29 May 1996 | 4/500 | |
| 25 Mar. 1997 | 5/500 | |
| 26 Mar. 1997 | 4.5/500 | |
| 27 Mar. 1997 | 4.5/500 | |
| 28 Mar. 1997 | 4.5/500 | |
| 7 Sep. 1997 | 4/500 | |
| 11 Sep. 1997 | 5/500 | |
| 26 Dec. 1997 | 4/500 | |
| 15 Jun. 1998 | 5/500 | |

After the 10 self-injections, the inventor determined there were no notable or irreversible side effects when injection 5 cc of pure garlic juice diluted in 500 cc of normal saline into a 70 kg person. At this point, the inventor decided to extend the research to willing and properly informed volunteers. The inventor initiated human trials of IV injection of garlic solution with willing volunteers (who reviewed and signed approvals to participate) on the 24 Mar., 1999, and tests continued for approximately 2 years.

4. Injection Results, Human Trials on Volunteers.

The volunteers were individuals who experienced recurrent outbreaks or manifestations of blisters on or around the mouth from the herpes virus. All volunteers were 20 to 50 years old, all volunteers were assessed to verify they had no systemic diseases, and it was determined that all volunteers would come in for initiation of the process on the first day of manifestation of blisters.

The volunteers were randomly divided into three groups: Group A; Group B; and Group C, and the testing was not blind because the volunteers could identify which individuals received the garlic solution. A total of 4 volunteer patients had genital herpes. Two of these patients were randomly assigned to Group A (patients 22 and 37,) one of these patients was randomly assigned to Group B (patient 29), and the last of these patients was randomly assigned to Group C. The patient with genital herpes who was placed in the control Group C dropped out of the program and that patient's results are not reported below. Each group received a different treatment, and the treatment started when they came in on the first day of blister manifestation. Group A received 100 milligrams (mg) of hydrocortisone by IV one hour before W injection of the garlic solution. Group B received IV injection of the garlic solution, but no hydrocortisone. Group C received no treatment. The first volunteer who came in with blisters was placed in Group A and first received IV hydrocortisone and IV garlic solution one hour later. The second volunteer who came in with active blisters was placed in Group B and received an IV garlic solution injection. The third patient who came in with active blisters was placed in Group C and received no treatment, and this sequential group assignment process was repeated for all the volunteers.

The garlic solution for all IV injections was prepared by mixing 0.065 cc of pure garlic juice for each kilogram of weight of the patient in 500 cc of normal saline. Therefore, the concentration of the garlic solution would vary somewhat depending on the weight of the patient. For all the patients the following data was observed are recorded: (1) duration of growth of the vesicles from the first manifestation to stopping their growth, which is when the blisters began to show drying and appear wrinkled; (2) duration of time from the beginning of the burning and itching sensation to the end of the burning and itching sensation, as reported by the volunteers, and this period matched the duration of the growth from the first manifestation to stopping the growth, so it is not separately reported here; and (3) duration of time from the injection to the time when the final crusts would fall off.

In all cases, the growth of the blisters stopped when the garlic solution was injected. The testing was conducted over a period of 2 years, and a total of 82 volunteer patients were seen. Patients were allowed to drop out of the program, and they would be replaced when they dropped out. When the test was completed, there were 28 volunteer patients in Group A, 29 volunteer patients in Group B, and 25 volunteer patients in Group C. Patients were observed at the testing facility for 48 hours after an injection. The patients were also cared for during the 48 hour observation period.

There were no notable differences in the results for Groups A and B, except that some of the Group B patients did have a stronger adverse reaction to the injection, such as more severe nausea or vomiting. Some of these patients had vesicles or blisters of the genital organs, and some patients had oral blisters. All patients in Groups A and B reported the end of burning, itching, and tingling in the blisters within about 6 hours. The blisters of all patients in Groups A and B stopped growing at the time of the garlic solution injection, and drying and wrinkling of the vesicles was clearly visible within 20 to 24 hours after the injection. The crusts from the blisters fell off after 4-5 days from the time of the injection for all patients in Groups A and B. Those patients with genital blisters were cured with essentially identical healing times as for the oral blisters. No differences in treatment or efficacy were seen between the oral or genital blisters.

In the control Group C, the blisters grew with burning, itching, and tingling for 3 to 5 days, and then gradually stopped. The crusts from the blisters fell off after 6 to 13 days in control Group C. After the completion of the test, the volunteer patients in Group C were allowed to receive IV injections of the garlic solution with hydrocortisone (as for Group A), and the patients who elected to do this are referred to as Group D. All subsequent testing used hydrocortisone as a precaution for prevention of any allergic reactions. The results for the Group D patients can be compared against the same individual when that individual received no treatment as a member of control Group C. The patient numbers were retained when patients moved from Group C to Group D, so the identity of individuals who served as both an experimental test subject and a control test subject can be determined by referring to the patient number. The results for Group D were consistent with the results for Groups A and B.

The members of Groups A, B, and D have reduced blister recurrence frequency compared to before the treatment. Also, recurrences are in different locations than before or during the treatment. It appears the recurrences after treatment with garlic solution injection are not the same infection that was treated, but rather a new re-infection. The following tables document the test results discussed above.

TABLE 3

Group A. These volunteers received 100 mg hydrocortisone by IV followed by 0.065 cc pure garlic juice per kg of patient weight, dissolved in 500 cc of normal saline, by IV.

| Patient # | Age | Gender | Weight (kg) | cc garlic juice injected | Days from blister manifestation to end of growth | Days from injection to crusts falling off | Days from blister manifestation to crusts falling off |
|---|---|---|---|---|---|---|---|
| 1 | 32 | M | 75 | 4.8 | 1 | 3.5 | 4.5 |
| 4 | 27 | M | 67 | 4.4 | 1.5 | 4 | 5.5 |
| 7 | 43 | M | 83 | 5.3 | 1 | 4 | 5 |
| 10 | 39 | M | 79 | 5.0 | 1 | 4 | 5 |
| 13 | 37 | F | 65 | 4.2 | 1 | 4 | 5 |
| 16 | 45 | M | 80 | 5.2 | 1 | 5 | 6 |
| 19 | 25 | F | 64 | 4.0 | 1 | 4 | 5 |
| 22 | 33 | M | 73 | 4.7 | 2 | 4.5 | 6.5 |
| 25 | 31 | M | 69 | 4.5 | 1 | 4 | 5 |
| 28 | 31 | M | 78 | 5.0 | 1 | 4 | 5 |
| 31 | 42 | F | 84 | 5.4 | 1 | 4 | 5 |
| 34 | 35 | M | 77 | 5.0 | 1 | 5 | 6 |
| 37 | 21 | F | 63 | 4.0 | 1.5 | 4.5 | 6 |
| 40 | 38 | M | 82 | 5.3 | 1 | 4 | 5 |
| 43 | 29 | M | 69 | 4.5 | 1 | 4.5 | 5.5 |
| 46 | 41 | M | 70 | 4.5 | 1 | 4 | 5 |
| 49 | 30 | F | 67 | 4.3 | 1 | 4 | 5 |
| 52 | 44 | M | 78 | 5.0 | 1 | 4 | 5 |
| 55 | 37 | F | 71 | 4.5 | 1.5 | 4 | 5.5 |
| 58 | 42 | M | 67 | 4.3 | 1 | 4 | 5 |
| 61 | 29 | F | 65 | 4.2 | 1 | 3.5 | 4.5 |
| 64 | 36 | F | 76 | 4.9 | 1 | 4.5 | 5.5 |
| 67 | 45 | M | 81 | 5.2 | 1.5 | 4 | 5.5 |
| 70 | 41 | M | 77 | 5.0 | 1 | 4 | 5 |
| 73 | 34 | M | 73 | 4.7 | 1 | 4.5 | 5.5 |
| 76 | 26 | M | 69 | 4.4 | 1.5 | 4 | 5.5 |
| 79 | 32 | F | 67 | 4.3 | 1 | 4 | 5 |
| 82 | 34 | M | 78 | 5.0 | 1 | 4 | 5 |
| Mean | | | | | | 4.13 | 5.25 |

TABLE 4

Group B. These volunteers received 0.065 cc pure garlic juice per kg of patient weight, dissolved in 500 cc of normal saline, by IV.

| Patient # | Age | Gender | Weight (kg) | cc garlic juice injected | Days from blister manifestation to end of growth | Days from injection to crusts falling off | Days from blister manifestation to crusts falling off |
|---|---|---|---|---|---|---|---|
| 2 | 47 | M | 80 | 5.2 | 1 | 4 | 5 |
| 5 | 34 | M | 75 | 4.8 | 1 | 4 | 5 |
| 8 | 29 | M | 67 | 4.3 | 1 | 3 | 4 |
| 11 | 37 | F | 78 | 5.0 | 1 | 4.5 | 5.5 |

TABLE 4-continued

Group B. These volunteers received 0.065 cc pure garlic juice per kg of patient weight, dissolved in 500 cc of normal saline, by IV.

| Patient # | Age | Gender | Weight (kg) | cc garlic juice injected | Days from blister manifestation to end of growth | Days from injection to crusts falling off | Days from blister manifestation to crusts falling off |
|---|---|---|---|---|---|---|---|
| 14 | 22 | F | 66 | 4.2 | 1.5 | 4 | 5.5 |
| 17 | 45 | M | 73 | 4.7 | 1 | 4 | 5 |
| 20 | 37 | M | 83 | 5.3 | 1 | 4 | 5 |
| 23 | 31 | F | 68 | 4.4 | 1 | 4 | 5 |
| 26 | 34 | M | 81 | 5.2 | 1.5 | 4.5 | 6 |
| 29 | 25 | F | 65 | 4.2 | 1 | 3 | 4 |
| 32 | 43 | M | 84 | 5.4 | 1 | 5 | 6 |
| 35 | 35 | M | 70 | 4.5 | 1 | 4 | 5 |
| 38 | 33 | M | 79 | 5.1 | 1 | 4 | 5 |
| 41 | 38 | F | 72 | 4.6 | 1 | 4.5 | 5.5 |
| 44 | 49 | F | 68 | 4.4 | 1 | 4 | 5 |
| 47 | 37 | M | 82 | 5.3 | 1 | 4 | 5 |
| 50 | 28 | M | 75 | 4.8 | 1 | 3 | 4 |
| 53 | 40 | F | 73 | 4.7 | 1 | 4.5 | 5.5 |
| 56 | 32 | M | 73 | 4.7 | 1 | 4 | 5 |
| 59 | 33 | M | 70 | 4.5 | 1 | 4 | 5 |
| 62 | 26 | M | 74 | 4.8 | 1 | 3.5 | 4.5 |
| 65 | 39 | M | 85 | 5.5 | 1 | 4 | 5 |
| 68 | 42 | M | 77 | 5.0 | 1 | 4 | 5 |
| 71 | 36 | F | 72 | 4.6 | 1.5 | 4 | 5.5 |
| 74 | 44 | M | 92 | 5.9 | 1 | 4.5 | 5.5 |
| 77 | 23 | M | 67 | 4.3 | 1 | 3.5 | 4.5 |
| 80 | 32 | F | 71 | 4.6 | 1 | 4 | 5 |
| 83 | 30 | M | 80 | 5.2 | 1 | 3 | 4 |
| 86 | 27 | M | 66 | 4.2 | 1 | 4 | 4 |
| Mean | | | | | | 3.95 | 5.00 |

TABLE 5

Group C. These volunteers received injection of garlic juice, and served as the control group.

| Patient # | Age | Gender | Weight (kg) | Days from blister manifestation to end of growth* | Days from blister manifestation to crusts falling off |
|---|---|---|---|---|---|
| 3 | 35 | F | 71 | 5 | 11 |
| 6 | 37 | M | 82 | 3 | 8 |
| 9 | 48 | M | 75 | 6 | 13 |
| 12 | 29 | M | 69 | 4 | 10 |
| 15 | 36 | F | 69 | 3 | 8 |
| 18 | 27 | M | 67 | 2 | 6 |
| 21 | 42 | M | 78 | 5 | 12 |
| 24 | 45 | M | 76 | 3 | 9 |
| 27 | 43 | F | 75 | 4 | 11 |
| 30 | 37 | M | 79 | 3 | 10 |
| 33 | 23 | F | 58 | 4 | 10 |
| 36 | 32 | F | 66 | 4 | 11 |
| 39 | 40 | F | 74 | 5 | 13 |
| 42 | 31 | M | 68 | 3 | 8 |
| 45 | 47 | M | 91 | 4 | 11 |
| 48 | 35 | M | 76 | 2 | 6 |
| 51 | 37 | F | 71 | 5 | 12 |
| 54 | 44 | M | 85 | 3 | 8 |
| 57 | 25 | M | 73 | 2 | 6 |
| 60 | 28 | F | 62 | 3 | 9 |
| 63 | 42 | M | 80 | 2 | 8 |
| 66 | 32 | F | 78 | 3 | 10 |
| 69 | 33 | M | 76 | 3 | 10 |
| 72 | 40 | M | 72 | 4 | 11 |
| 75 | 28 | M | 74 | 3 | 9 |
| Mean | | | | 3.52 | 9.6 |

*Determining when the growth of a blister stops is not very accurate for the control group, because some parts of the blisters would stop growing while other parts continued to grow. The measure is accurate for experimental groups because all growth stopped upon injection of the garlic solution.

TABLE 6

Group D. These volunteers received 0.065 cc pure garlic juice per kg of patient weight, dissolved in 500 cc of normal saline, by IV. The volunteers in this group were from the control Group C, and this testing was performed subsequent to the testing with Groups A, B, and C. Results for individuals with outbreaks both with and without the treatment can be seen by referring to the patient numbers, because patient numbers were retained between Groups C and D.

| Patient # | Age | Gender | Weight (kg) | cc garlic juice injected | Days from blister manifestation to end of growth | Days from injection to crusts falling off | Days from blister manifestation to crusts falling off |
|---|---|---|---|---|---|---|---|
| 6 | 37 | M | 82 | 5.3 | 1 | 3 | 4 |
| 9 | 48 | M | 75 | 4.8 | 1 | 5 | 6 |
| 12 | 29 | M | 69 | 4.5 | 1 | 4 | 5 |
| 15 | 36 | F | 69 | 4.5 | 1 | 3.5 | 4.5 |
| 21 | 42 | M | 78 | 5.0 | 1 | 4.5 | 5 |
| 27 | 43 | F | 75 | 4.8 | 1 | 4 | 5 |
| 30 | 37 | M | 79 | 5.1 | 1 | 4 | 5 |
| 33 | 23 | F | 58 | 3.7 | 1 | 4 | 5 |
| 42 | 31 | M | 68 | 4.4 | 1 | 3.5 | 4.5 |
| 45 | 47 | M | 91 | 5.9 | 1 | 4 | 5 |
| 48 | 35 | M | 76 | 4.9 | 1 | 4 | 5 |
| 51 | 37 | F | 71 | 4.6 | 1 | 4.5 | 5.5 |
| 57 | 25 | M | 73 | 4.7 | 1 | 3 | 4 |
| 60 | 28 | F | 62 | 4.0 | 1 | 4 | 5 |
| 63 | 42 | M | 80 | 5.2 | 1 | 3.5 | 4.5 |
| 69 | 33 | M | 76 | 4.9 | 1.5 | 4 | 5.5 |
| 75 | 28 | M | 74 | 4.8 | 1 | 4 | 5 |
| Mean | | | | | | 3.91 | 4.91 |

TABLE 7

Portions of Group C. These results are extracted from Table 5 for the volunteers who participated in Groups C and D, for direct comparison purposes.

| Patient # | Age | Gender | Weight (kg) | Days from blister manifestation to end of growth* | Days from blister manifestation to crusts falling off |
|---|---|---|---|---|---|
| 6 | 37 | M | 82 | 3 | 8 |
| 9 | 48 | M | 75 | 6 | 13 |
| 12 | 29 | M | 69 | 4 | 10 |

TABLE 7-continued

Portions of Group C. These results are extracted from Table 5 for the volunteers who participated in Groups C and 1), for direct comparison purposes.

| Patient # | Age | Gender | Weight (kg) | Days from blister manifestation to end of growth* | Days from blister manifestation to crusts falling off |
|---|---|---|---|---|---|
| 15 | 36 | F | 69 | 3 | 8 |
| 21 | 42 | M | 78 | 5 | 12 |
| 27 | 43 | F | 75 | 4 | 11 |
| 30 | 37 | M | 79 | 3 | 10 |
| 33 | 23 | F | 58 | 4 | 10 |
| 42 | 31 | M | 68 | 3 | 8 |
| 45 | 47 | M | 91 | 4 | 11 |
| 48 | 35 | M | 76 | 2 | 6 |
| 51 | 37 | F | 71 | 5 | 12 |
| 57 | 25 | M | 73 | 2 | 6 |
| 60 | 28 | F | 62 | 3 | 9 |
| 63 | 42 | M | 80 | 2 | 8 |
| 69 | 33 | M | 76 | 3 | 10 |
| 75 | 28 | M | 74 | 3 | 9 |
| Mean | | | | 3.47 | 9.47 |

5. Injection Results, Human Intentional Infection and Cure.

The inventor analyzed the test results, and decided to conduct an in vivo treatment test on tissue with a visible herpes infection. The recurrent herpetic whitlow infection recurs frequently and often the skin does not completely heal after an active blister. The recurrent herpetic whitlow infections can have lengthy outbreaks, which gives time to monitor the results. The fact that recurrent herpetic whitlow frequently recurs for lengthy periods, and the skin does not completely heal after an outbreak, makes recurrent herpetic whitlow a good condition to determine if the garlic juice injections simply treat an active outbreak, or completely cure the herpes infection. Recurrent herpetic whitlow is also less common that oral or genital herpes, and the fingers are not a preferred site for herpes infections so re-infection after the treatment is less likely. The inventor conducted this test by intentionally infecting himself with the herpes virus, verifying the infection was present and recurrent, and curing the infection with injections of garlic solution.

To begin the test, the inventor decided to infect his left thumb with the herpes virus. The inventor cleaned the medial side of his left thumb and active vesicles of a patient's lip with soap and warm water, and then rinsed them with sterile normal saline. The inventor then cut some blisters on the patient's lip with a sterile scalpel, and then used the same scalpel with remaining residue from the blisters to make some shallow oblique cuts to the subcutaneous layer of the inventor's left thumb on the medial side. These cuts on the inventor's thumb were then covered be sterile wet gauze and latex for 24 hours.

The inventor noticed an itching and tingling feeling at the location of the cuts after about 10 days, and then a deep vesicle appeared that was extending to the surface of the skin. This vesicle was torn by scratching. In the following weeks more vesicles appeared, with associated itching and tingling sensations. A dermatologist confirmed the inventor had herpetic whitlow on his thumb using the Tzanck test. The inventor waited for 2 months and verified the herpetic whitlow infection was recurrent, or recurrent herpetic whitlow.

After verifying the infection was recurrent, the inventor initiated the treatment by orally taking 1.5 cc of pure garlic juice 3 times a day for 10 days. This did not atop the blister growth, and the infection remained recurrent. The inventor then applied cryotherapy with ice 3 times a day, for 15 minutes per application, for 3 consecutive days. This caused the blisters to subside, but the infected area never returned to a normal and healthy state, and the blisters recurred later. The inventor then applied garlic topically to the blisters 3 times a day for 3 consecutive days. This caused the blisters to subside, but they recurred later.

The inventor then simultaneously orally administered 1.5 cc of pure garlic juice 3 times a day for 10 days, and during the first 3 days the inventor also applied cryotherapy and topical garlic applications to the blisters, as described above. The blisters subsided, but recurred again with inflammation of the skin. When inactive, the external layer of skin appeared thin, wrinkled, and sometimes exfoliated. This area of the inventor's thumb was approximately the same size as a bean, or about 8 millimeters (mm) by 15 mm, and it had a frosted white appearance in depth but it did not protrude or bulge out. The oral and topical efforts at treatment described above were conducted over a 9 month period, and the recurrent herpetic whitlow remained recurrent, or kept coming back. The inventor confirmed the recurrent infection was herpetic whitlow with the Tzanck test.

The inventor then decided to investigate injections of garlic solution as a treatment method. On 3 May 2006, the inventor intravenously injected himself with 5 cc of pure garlic juice dissolved in 500 cc of normal saline. Beginning on 4 May 2006, the inventor noticed a reduction of the tingling and itching, and after 6 weeks there were no visible signs of recurrent herpetic whitlow on the inventor's thumb, and this location returned to a normal shape and appearance, as with a healthy thumb. There was no scar, no exfoliation, pain, itching, or tingling, and there has been no recurrence of the recurrent herpetic whitlow on the inventor's thumb at least through 4 Jan. 2013.

The inventor then found six volunteer patients with recurrent herpetic whitlow who agreed to take the garlic solution injections (on the condition the inventor would verify the safety by simultaneously taking the garlic solution injection himself, which the inventor agreed to do). These six volunteers were patients of dermatologists, and Tzanck testing verified all had herpetic whitlow, and there was no indication of any secondary infections. Five other patients who were verified to have recurrent herpetic whitlow agreed to participate in a control group.

These 6 volunteer patients with recurrent herpetic whitlow received IV injections of 0.065 cc pure garlic juice per kg of patient weight in 500 cc normal saline on 18 Nov. 2006. Inflammation and swelling for all 6 patients gradually reduced, and was no longer visible after 4 days. All 6 patients reported the pain, burning, tingling, and itching sensation decreased beginning the day after the injection. No new vesicles appeared on any of the 6 patients, and the existing vesicles that were visible on the surface of the skin were eliminated in the first week. Existing vesicles from below the surface of the skin rose and exfoliated gradually over a period of 3 to 4 weeks, and after 6 to 8 weeks there was no sign of recurrent herpetic whitlow. After the 8 week period, all 6 patients reported no further signs of recurrent herpetic whitlow and no recurrence of the infection through at least 1 Nov. 2012.

The five patients who agreed to participate in the control group continue to have signs of recurrent herpetic whitlow with periodic outbreaks. Based on these results, the inventor has concluded that recurrent herpetic whitlow can be treated and cured by IV injection of garlic juice, and even by a single IV injection of garlic juice.

6. Human Test Results for Other Conditions.

Three patients infected with malaria volunteered to receive injections of garlic solution to determine the results. The malaria infections were verified by consultation with the patient's physician. These three patients received IV injections of 0.065 cc of pure garlic juice per kilogram of weight of the patient, where the garlic juice was dissolved in at least 500 cc of normal saline, and sometimes more saline. The IV injections were administered once per day for four consecutive days, where the injections were at approximately the same time of day. The three patients left the care of the inventor after 6 days, but the patient's physician verified there was no sign or symptom of malaria for at least 6 months after the injections. The inventor used 4 injections spread over 4 days to cover the life cycle of the malaria parasite in the body.

Two patients with multiple sclerosis (MS) volunteered and received one IV injection of 0.065 cc of pure garlic juice per kilogram of weight of the patient, where the garlic juice was dissolved in 500 cc of normal saline. The MS condition was verified by a neurologist treating the patients. These patients were followed for 6 months, and they reported feeling better and having improved, motion after the injection. The garlic solution was given to the MS patients based on the theory that MS may be caused by HSV-6.

Three patients living in the Iranian city of Esfahan volunteered for treatment of their cutaneus leishmaniasis condition. Cutaneus leishmaniasis is a skin infection caused by single celled parasites that produces large boils or sores. These three patients were treated on the first day with an IV injection of 0.065 cc of pure garlic juice per kilogram of weight of the patient, where the garlic juice was dissolved in 500 cc of normal saline. The boils were also treated topically with raw garlic 3 times a day, beginning on the same day as the injection and continuing for a total of 5 consecutive days. The sores healed rapidly, with no prolonged effects.

Some vaginal infections were cured by topical application of garlic by shooting 20% garlic solution into the vaginal cavity. Preliminary laboratory tests were performed on the infectious agents to determine which patients were amenable to treatment with garlic.

Two patients with grand mal epilepsy were given one IV injection of garlic solution per day for two consecutive days. The IV injection was 0.065 cc of pure garlic juice per kilogram of weight of the patient, where the garlic juice was dissolved in 500 cc of normal saline. The patients stated that they felt better after the injection, and the number and intensity of epileptic seizures was reduced.

Three volunteer male patients with kidney and urinary tract infections were found, where the infections were resistant to antibiotic medications. These infections were bacterial, and they were one example of an antibiotic resistant bacterial infection. These patients received 0.065 g garlic juice per kg of patient weight, diluted in normal saline, by IV injection. These patients also received 5 cc of 10% garlic solution in normal saline injected into the urethra such that 4 cc were injected into the bladder and 1 cc was injected into the urethra. On the $1^{st}$ and $2^{nd}$ day, both the IV and urethra injections were administered. On the $3^{rd}$ day, only the IV injection was administered. The patients were completely cured in about 4-5 days after the $1^{st}$ garlic juice injections, as verified by urinary analysis.

Other conditions that have shown promise, based on experimental use and observation and reports from human patients, include:

a) The treatment of cystits in women by injection of 0.5 cc of a 10% solution of pure garlic juice in normal saline into the urinary duct. The patients reported relief of pain and discomfort within 15 minutes of the injection.

b) Many dysenteries were successfully treated orally.

c) Various skin infections, including acne, were successfully treated by topical application and/or IV injection. Dilute garlic solutions were not as effective as pure garlic juice for topical treatment of acne.

d) After drainage of an abscess, a 10% garlic solution was injected into the abscess space and there was no extension of that abscess.

e) IV injections of garlic solutions, as described above, have reduced the healing period for the common cold and influenza.

f) Dilute solutions of garlic juice were used for burns for maintenance and prevention of infections.

g) Many patients have stated relief from a wide variety of afflictions after an injection of a garlic solution. The cause of these afflictions was never determined, but the afflictions that were reported as improved include chronic fatigue, mild depression, mild amnesia, nightmares, and vertigo.

The inventor believes the use of garlic juice is an initial step in the treatment of a wide variety of infections, and can open the door to an improved state of health care. While the invention has been described with respect to a limited number of embodiments, those skilled in the art, having benefit of this disclosure, will appreciate that other embodiments can be devised which do not depart from the scope of the invention as disclosed here. According the scope of the invention should be limited only by the attached claims,

What is claimed is:

1. A method of treating herpes comprising:
   (a) identifying a patient with a recurrent herpetic whitlow infection;
   (b) obtaining a garlic solution comprising garlic juice and a solvent;
   (c) injecting the garlic solution into the patient.

2. The method of claim 1 where the solvent comprises normal saline.

3. The method of claim 1 where the garlic solution is injected into, the patient while the herpetic infection is active.

4. The method of claim 1 where the garlic juice is extracted from raw garlic cloves, and where the raw garlic cloves are sterilized before the garlic juice is extracted.

5. The method of claim 1 where (c) further comprises injection the garlic solution into the patient intravenously.

6. The method of claim 5 further comprising intravenously injecting hydrocortisone into the patient at the same location as the garlic solution.

7. The method of claim 6 where the hydrocortisone is injected prior to the garlic solution.

8. The method of claim 1 where the garlic solution comprises at least 100 grams of water per gram of garlic juice.

9. The method of claim 1 further comprising:
   determining a weight of the patient; and
   preparing the garlic solution for injection such that the patient receives at least 0.065 grams of garlic juice per kilogram of the patient's weight.

10. The method of claim 1 where the garlic juice is extracted from raw garlic.

11. The method of claim 1 further comprising repeatedly injecting the patient with the garlic solution.

* * * * *